United States Patent [19]

Peterson

[11] 4,160,102

[45] Jul. 3, 1979

[54] ω-ARYL-INTER-OXA-9-DEOXY-PGD₁ COMPOUNDS

[75] Inventor: David C. Peterson, Portage, Mich.

[73] Assignee: The Upjohn Company, Kalamazoo, Mich.

[21] Appl. No.: 903,625

[22] Filed: May 8, 1978

Related U.S. Application Data

[62] Division of Ser. No. 809,249, Jun. 23, 1977, which is a division of Ser. No. 614,244, Sep. 17, 1975.

[51] Int. Cl.² ............................................. C07C 177/00
[52] U.S. Cl. ...................................... 560/53; 562/463; 562/464
[58] Field of Search .................... 560/53; 562/463, 464

[56] References Cited

U.S. PATENT DOCUMENTS 3,878,239  4/1975  Hayashi et al. ..................... 562/508

Primary Examiner—Paul J. Killos
Attorney, Agent, or Firm—Robert A. Armitage

[57] ABSTRACT

Prostaglandin analogs with the following cyclopentane ring structure:

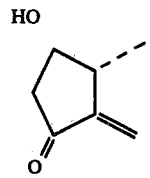

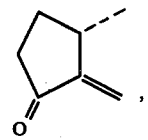

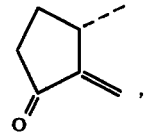

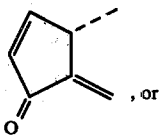

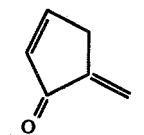

are disclosed along with intermediates useful in their preparation and processes for their preparation. These analogs are useful for some of the same pharmacological purposes as the prostaglandins, particularly and especially as blood platelet aggregation inhibitors.

25 Claims, No Drawings

ω-ARYL-INTER-OXA-9-DEOXY-PGD$_1$ COMPOUNDS

The present application is a divisional application of Ser. No. 809,249, filed June 23, 1977, now U.S. Pat. No. 4,142,052 issued Feb. 27, 1979; which is a divisional application of Ser. No. 614,244, filed Sept. 17, 1975, now pending. Likewise, U.S. Ser. No. 809,248, filed June 23, 1977, now U.S. Pat. No. 4,099,014 issued on July 4, 1978, is a divisional application of Ser. No. 614,244.

The present invention relates to prostaglandin analogs for which the essential material constituting a disclosure therefor is incorporated by reference here from U.S. Pat. No. 4,099,014.

I claim:

1. A prostaglandin analog of the formula

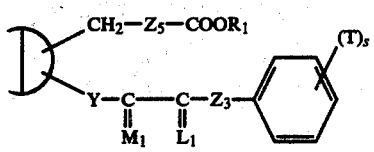

wherein D is

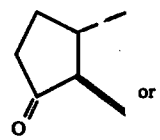

or

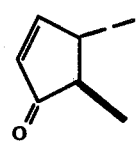

wherein
Y is cis-CH=CH—, trans-CH=CH—, or —CH$_2$CH$_2$—;
wherein Z$_5$ is
(1) —CH$_2$—O—CH$_2$—(CH$_2$)$_g$—CH$_2$—,
(2) —(CH$_2$)$_2$—O—(CH$_2$)$_g$—CH$_2$—, or
(3) —(CH$_2$)$_3$—O—(CH$_2$)$_g$—,
wherein g is one, 2, or 3;
wherein M$_1$ is

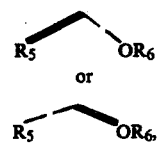

or

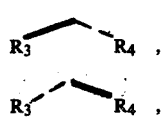

wherein
R$_5$ and R$_6$ are hydrogen or methyl, with the proviso that one of R$_5$ and R$_6$ is methyl only when the other is hydrogen;
wherein L$_1$ is

or a mixture of

and wherein
R$_3$ and R$_4$ are hydrogen, methyl, or fluoro, being the same or different, with the proviso that one of R$_3$ and R$_4$ is hydrogen or fluoro only when the other is hydrogen or fluoro;
wherein
Z$_3$ is oxa or methylene;
wherein
T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that Z$_3$ is oxa only when R$_3$ and R$_4$ are hydrogen or methyl, being the same or different; and
wherein
R$_1$ is hydrogen, alkyl of one to 12 carbon atoms, inclusive, cycloalkyl of 3 to 10 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation; with the further proviso that D is

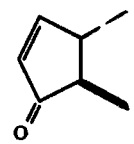

only when Y is —CH$_2$CH$_2$—.

2. A compound according to claim 1, wherein M$_1$ is

3. A compound according to claim 1, wherein M$_1$ is

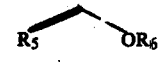

4. A compound according to claim 3, wherein D is

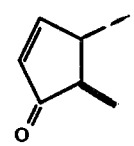

and Y is —CH$_2$CH$_2$—.

5. A compound according to claim 4, wherein Z$_3$ is methylene.

6. A compound according to claim 5, wherein s is zero or one and T is chloro, fluoro, or trifluoromethyl.

7. A compound according to claim 6, wherein g is one.

8. A compound according to claim 7, wherein $R_5$ and $R_6$ are both hydrogen.

9. A compound according to claim 8, wherein $R_3$ and $R_4$ are both hydrogen.

10. 5-Oxa-17-phenyl-18,19,20-trinor-13,14-dihydro-9,10-didehydro-9-deoxy-PGD$_1$, a compound according to claim 9.

11. A compound according to claim 4, wherein $Z_3$ is oxa.

12. A compound according to claim 11, wherein s is zero or one and T is chloro, fluoro, or trifluoromethyl.

13. A compound according to claim 3, wherein D is

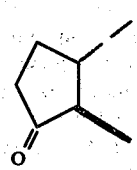

14. A compound according to claim 13, wherein $Z_3$ is methylene.

15. A compound according to claim 14, wherein s is zero or one and T is chloro, fluoro, or trifluoromethyl.

16. A compound according to claim 15, wherein g is one.

17. A compound according to claim 16, wherein $R_5$ and $R_6$ are both hydrogen.

18. A compound according to claim 17, wherein $R_3$ and $R_4$ are both hydrogen.

19. 5-Oxa-17-phenyl-18,19,20-trinor-9-deoxy-PGD$_1$, a compound according to claim 18.

20. A compound according to claim 13, wherein $Z_3$ is oxa.

21. A compound according to claim 20, wherein s is zero or one and T is chloro, fluoro, or trifluoromethyl.

22. A compound according to claim 21, wherein g is one.

23. A compound according to claim 22, wherein $R_5$ and $R_6$ are both hydrogen.

24. A compound according to claim 23, wherein $R_3$ and $R_4$ are both hydrogen.

25. 5-Oxa-16-phenoxy-17,18,19,20-tetranor-9-deoxy-PGD$_1$, a compound according to claim 24.

* * * * *

UNITED STATES PATENT OFFICE
CERTIFICATE OF CORRECTION

Patent No. 4,160,102    Dated 3 July 1979

Inventor(s) David C. Peterson

It is certified that error appears in the above-identified patent and that said Letters Patent are hereby corrected as shown below:

In the abstract, the first formula should read

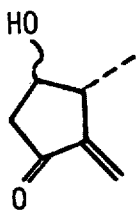

Signed and Sealed this

Twentieth Day of November 1979

[SEAL]

Attest:

RUTH C. MASON
Attesting Officer

LUTRELLE F. PARKER
Acting Commissioner of Patents and Trademarks